(12) United States Patent
Yamamoto

(10) Patent No.: US 9,694,076 B2
(45) Date of Patent: Jul. 4, 2017

(54) VESICLE COMPOSITION

(71) Applicant: KAO CORPORATION, Tokyo (JP)

(72) Inventor: Yumiko Yamamoto, Taito-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/049,233

(22) Filed: Feb. 22, 2016

(65) Prior Publication Data

US 2016/0166698 A1 Jun. 16, 2016

Related U.S. Application Data

(62) Division of application No. 14/008,997, filed as application No. PCT/JP2012/058674 on Mar. 30, 2012, now abandoned.

(30) Foreign Application Priority Data

Mar. 31, 2011 (JP) ................. 2011-078467

(51) Int. Cl.
| | |
|---|---|
| A61K 8/14 | (2006.01) |
| A61K 8/63 | (2006.01) |
| A61K 8/68 | (2006.01) |
| A61Q 19/00 | (2006.01) |
| A61K 47/18 | (2017.01) |
| A61K 8/36 | (2006.01) |
| A61K 8/41 | (2006.01) |
| A61K 8/44 | (2006.01) |
| A61K 47/02 | (2006.01) |
| A61K 47/12 | (2006.01) |

(52) U.S. Cl.
CPC .............. *A61K 47/18* (2013.01); *A61K 8/14* (2013.01); *A61K 8/361* (2013.01); *A61K 8/41* (2013.01); *A61K 8/44* (2013.01); *A61K 8/63* (2013.01); *A61K 8/68* (2013.01); *A61K 47/02* (2013.01); *A61K 47/12* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,372,814 A | 12/1994 | Mizushima et al. | |
| 5,776,488 A | 7/1998 | Mori et al. | |
| 6,306,848 B1 | 10/2001 | Fujimura et al. | |
| 6,348,200 B1 | 2/2002 | Nakajima et al. | |
| 7,846,969 B2 | 12/2010 | Yamamoto et al. | |
| 2002/0022611 A1 | 2/2002 | Fujimura et al. | |
| 2004/0122103 A1 | 6/2004 | Hoshino et al. | |
| 2005/0152865 A1 | 7/2005 | Yamamoto et al. | |
| 2005/0287095 A1 | 12/2005 | Fujiwara | |
| 2009/0220584 A1 | 9/2009 | Goodwin et al. | |
| 2011/0263714 A1 | 10/2011 | Okubo | |
| 2012/0114721 A1 | 5/2012 | Matsumoto et al. | |

FOREIGN PATENT DOCUMENTS

| | | |
|---|---|---|
| CN | 1665478 A | 9/2005 |
| CN | 101686911 A | 3/2010 |
| CN | 101827578 A | 9/2010 |
| JP | 5 501714 | 4/1993 |
| JP | 5 294989 | 11/1993 |
| JP | 7-10731 A | 1/1995 |
| JP | 8 225428 | 9/1996 |
| JP | 9-87130 A | 3/1997 |
| JP | 9-263511 A | 10/1997 |
| JP | 11 130651 | 5/1999 |
| JP | 3126193 B2 | 1/2001 |
| JP | 2001 48721 | 2/2001 |
| JP | 2005-281293 A | 10/2005 |
| JP | 2006 335651 | 12/2006 |
| JP | 2008-19230 A | 1/2008 |
| JP | 2008 31142 | 2/2008 |
| JP | 2009 518297 | 5/2009 |

(Continued)

OTHER PUBLICATIONS

International Search Report Issued Jun. 19. 2012 in PCT/JP12/058674 filed Mar. 30. 2012.

(Continued)

*Primary Examiner* — Theodore R West
(74) *Attorney, Agent, or Firm* — Oblon, McClelland, Maier & Neustadt, L.L.P.

(57) ABSTRACT

The present invention is to provide a vesicle composition comprising the following components (A), (B) and (C):

(A) 0.0001 to 20 mass % of an organic acid represented by general formula (1):

wherein $R^1$ represents a natural sterin having a single hydroxy group or a hydrogenated product thereof or a residue which remains after a hydrogen atom is removed from the hydroxy group of bile acid, $R^2$ represents a divalent hydrocarbon group having 1 to 24 carbon atoms, M represents a hydrogen atom, an alkali metal, an alkali earth metal, ammonium, an alkanolammonium having 2 to 9 carbon atoms in total, an alkylammonium or alkenylammonium having 1 to 22 carbon atoms in total, pyridinium substituted with an alkyl group or alkenyl group having 1 to 18 carbon atoms or a basic amino acid, (B) 0.0001 to 10 mass % of a sphingosine, and (C) water, and having a pH of 2 to 11.

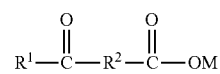

(1)

13 Claims, No Drawings

(56) References Cited

FOREIGN PATENT DOCUMENTS

| TW | I329023 B | 8/2010 |
|----|-----------|--------|
| WO | 95 24201 | 9/1995 |
| WO | 2004 004676 | 1/2004 |
| WO | WO 2005/063212 A1 | 7/2005 |
| WO | 2008 026349 | 3/2008 |
| WO | 2009/019891 A1 | 2/2009 |
| WO | WO 2009/019891 A1 | 2/2009 |
| WO | 2011/004589 A1 | 1/2011 |
| WO | WO 2011/007525 A1 | 1/2011 |

OTHER PUBLICATIONS

Extended European Search Report issued Oct. 20, 2014 in Patent Application No. 12765052.1.
International Preliminary Report on Patentability and Written Opinion issued Oct. 17, 2013 in PCT/JP2012/058674 (submitting English translation only).
Takahashi et al., "Multilamellar Vesicles Formed from Monoglycerides, Physico-chemical Properties and Stability", Fragrance Journal, vol. 34, No. 11, Nov. 2006, pp. 85-89 (w/ machine-generated English translation).

VESICLE COMPOSITION

REFERENCE TO RELATED APPLICATIONS

This application is a division of U.S. patent application Ser. No. 14/008,997, filed Sep. 30, 2013; which is a 371 of PCT/JP2012/058674, filed Mar. 30, 2012, the disclosures of which are incorporated herein by reference in their entireties. This application claims priority to Japanese Patent Application No. 2011-078467, filed Mar. 31, 2011, the disclosure of which is incorporated herein by reference in its entirety.

FIELD OF THE INVENTION

The present invention relates to a vesicle composition.

BACKGROUND OF THE INVENTION

Vesicles or liposomes made of lipid are mostly constituted of an amphipathic substance, phospholipid (Patent Literature 1, Patent Literature 2, Patent Literature 3, and Patent Literature 4). Phospholipid is a major structural component of natural membrane and a lipid vesicle is suitable as a model for studying the natural membrane.

However, phospholipid per se is unstable and decomposes in the absence of an antioxidant. Also high cost in synthesis and purification is a problem. A vesicle per se made of an unstable substance is also unstable. This is also a problem.

In the case of a cationic or an anionic vesicle composition, the vesicle breaks down if pH changes, and becomes no longer stable. If the vesicle is charged with active ingredients, these are released from the vesicle. For example, even if a high-crystalline component like a ceramide, which effectively works for skin roughness, is stabilized in a vesicle, if the vesicle is broken down by the effect of pH, a ceramide is crystallized and loses the effect. Furthermore, an active ingredient stable in a vesicle, if it is released from the vesicle by breakage due to the effect of pH, is decomposed and the effect cannot be obtained. These problems occur.

CITATION LIST

Patent Literature

[Patent Literature 1] JP-A-11-130651
[Patent Literature 2] JP-A-2006-335651
[Patent Literature 3] JP-A-2001-48721
[Patent Literature 4] JP-A-2009-518297

SUMMARY OF THE INVENTION

The present invention is to provide a vesicle composition comprising the following components (A), (B) and (C):

(A) 0.0001 to 20 mass % of an organic acid represented by general formula (1):

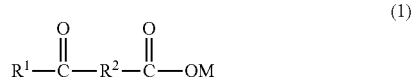

wherein $R^1$ represents a natural sterin having a single hydroxy group or a hydrogenated product thereof or a residue which remains after a hydrogen atom is removed from the hydroxy group of bile acid, $R^2$ represents a divalent hydrocarbon group having 1 to 24 carbon atoms, M represents a hydrogen atom, an alkali metal, an alkali earth metal, ammonium, an alkanolammonium having 2 to 9 carbon atoms in total, an alkylammonium or alkenylammonium having 1 to 22 carbon atoms in total, pyridinium substituted with an alkyl group or alkenyl group having 1 to 18 carbon atoms or a basic amino acid, (B) 0.0001 to 10 mass % of a sphingosine, and
(C) water, and
having a pH of 2 to 11.

Effects of the Invention

The vesicle composition of the present invention is stable and excellent in storage stability even if the surface charge of the vesicle changes by pH and further adaptable to the skin. In the present invention, the term "adaptable to the skin" refers to the feel that the composition is immediately absorbed upon applying to the skin, in other words, refers to the feel that the composition enters into the skin with little feel that the composition long remains on the skin surface.

EMBODIMENTS FOR CARRYING OUT THE INVENTION

The present invention relates to a vesicle composition.

The present inventor found that if a specific organic acid and sphingosine are used, a vesicle composition excellent in stability against pH change and storage stability can be obtained.

The organic acid as component (A) to be used in the present invention is represented by general formula (1).

In general formula (1), examples of the natural sterin having a single hydroxy group and represented by $R^1$ include cholesterol, stigmasterol, sitosterol, campesterol, lanosterol and ergosterol. Of them, cholesterol is preferable.

Furthermore, in general formula (1), $R^2$ is a divalent hydrocarbon group having 1 to 24 carbon atoms. For example, a linear or branched alkylene group or alkenylene group is mentioned and $R^2$ is preferably a group represented by the following formula:

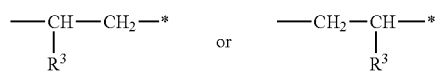

wherein $R^3$ represents a linear or branched alkyl group or alkenyl group having 6 to 20 carbon atoms (note that, in any of the above formulae, at the side represented by *, a carboxyl group is to be bonded).

Examples of $R^3$ include a linear or branched 2-hexenyl group, 2-octenyl group, 2-decenyl group, 2-dodecenyl group, 2-tetradecenyl group, 2-hexadecenyl group, 2-octadecenyl group, a 2-eicocenyl group, hexyl group, octyl group, decyl group, dodecyl group, tetradecyl group, hexadecyl group, octadecyl group and eicosyl group. Of them, a 2-tetradecenyl group, a 2-hexadecenyl group, a 2-octadecenyl group, a 2-eicocenyl group, a tetradecyl group, a hexadecyl group, an octadecyl group and an eicosyl group are preferable.

Such an organic acid (1) can be obtained, for example, by reacting a sterin with an alkenyl succinic anhydride or an alkyl succinic anhydride and performing neutralization with an alkaline substance, if necessary, in accordance with the method described in JP-A-5-294989.

As component (A), one or two or more can be used. Component (A) can be contained in an amount of 0.0001 to 20 mass % in the total composition, preferably 0.001 to 15 mass % and more preferably 0.01 to 10 mass %. If the content falls within the range, a vesicle composition can be obtained without impairing a sense of use.

As the sphingosine as component (B), one or two or more represented by general formula (2) are mentioned.

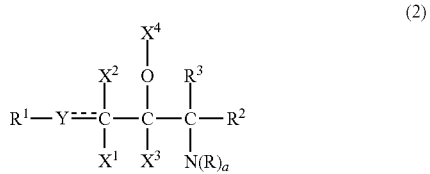

(2)

wherein $R^1$ represents a linear alkyl group having 4 to 30 carbon atoms, which is optionally substituted with a hydroxyl group, a carbonyl group or an amino group; Y represents a methylene group, a methine group or an oxygen atom; $X^1$, $X^2$, and $X^3$ each independently represent a hydrogen atom, a hydroxyl group or an acetoxy group; $X^4$ represents a hydrogen atom, an acetyl group or a glyceryl group, or forms an oxo group together with the adjacent oxygen atom, with the proviso that when Y is a methine group, either one of $X^1$ and $X^2$ is a hydrogen atom and the other is not present, and when $X^4$ forms an oxo group, $X^3$ is not present; $R^2$ and $R^3$ independently represent a hydrogen atom, a hydroxyl group, a hydroxymethyl group or an acetoxymethyl group; symbol a represents an integer of 2 or 3; each of $(R)_a$ represents a hydrogen atom or an amidino group, or represents a linear alkyl group having 1 to 8 carbon atoms in total, which optionally has a substituent selected from the group consisting of a hydroxyl group, a hydroxyalkoxy group, an alkoxy group and an acetoxy group; and the broken line indicates that the bond may be an unsaturated bond.

wherein $R^1$ represents a linear alkyl group having 4 to 30 carbon atoms which is optionally substituted with a hydroxyl group, a carbonyl group or an amino group, and preferably a linear alkyl group having 7 to 24 carbon atoms which is optionally substituted with a hydroxyl group. Furthermore, a linear alkyl group having 10 to 24 carbon atoms and a linear alkyl group having 10 to 24 carbon atoms in which a carbon atom to be bonded to Y in general formula (2) has a hydroxyl group are preferable. Specifically, a tridecyl group, a tetradecyl group, a pentadecyl group, a hexadecyl group, a 1-hydroxytridecyl group and a 1-hydroxypentadecyl group are preferable.

Y represents any one of a methylene group ($CH_2$), a methine group (CH) and an oxygen atom.

$X^1$, $X^2$ and $X^3$ each independently represent a hydrogen atom, a hydroxyl group or an acetoxy group, $X^4$ represents a hydrogen atom, an acetyl group, a glyceryl group, a substituent which forms an oxo group together with the adjacent oxygen atom. It is further preferable that 0 to 1 of $X^1$, $X^2$ and $X^3$ is a hydroxyl group and the remaining ones are hydrogen atoms and $X^4$ is a hydrogen atom. Note that, if Y is a methine group, only either one of $X^1$ and $X^2$ is a hydrogen atom and the other is not present. Furthermore, if $X^4$ forms an oxo group, $X^3$ is not present.

$R^2$ and $R^3$ each independently represent a hydrogen atom, a hydroxyl group, a hydroxymethyl group or an acetoxymethyl group and further preferably $R^3$ is a hydrogen atom.

Furthermore, symbol a represents an integer of 2 or 3; if symbol a is 2, R represents $R^4$ and $R^5$; whereas if symbol a is 3, R represents $R^4$, $R^5$ and $R^6$.

$R^4$, $R^5$ and $R^6$ each independently represent a hydrogen atom or an amidino group, or represent a linear alkyl group having 1 to 8 carbon atoms in total, which optionally has a substituent selected from the group consisting of a hydroxyl group, a hydroxyalkoxy group, an alkoxy group and an acetoxy group. Herein, as the hydroxyalkoxy group by which the alkyl group may be substituted, a linear or branched hydroxyalkoxy group having 1 to 7 carbon atoms is preferable. Furthermore, as the alkoxy group, a linear or branched alkoxy group having 1 to 7 carbon atoms is preferable. Examples of $R^4$, $R^5$ and $R^6$ include a hydrogen atom; linear or branched alkyl groups such as methyl, ethyl, propyl, 2-ethylhexyl and isopropyl; alkenyl groups such as vinyl and allyl; an amidino group; and hydrocarbon groups having 1 to 8 carbon atoms in total and having 1 to 6 substituents selected from the group consisting of a hydroxyl group, a hydroxyalkoxy group and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl and 1,1-bis(hydroxymethyl)-2-hydroxyethyl.

Further preferably as $R^4$, $R^5$ and $R^6$, a hydrogen atom or an alkyl group which optionally has 1 to 3 substituents selected from the group consisting of a hydroxyl group and a hydroxyalkoxy group, such as methyl, 2-hydroxyethyl, 1,1-dimethyl-2-hydroxyethyl, 1,1-bis(hydroxymethyl)ethyl, and 2-(2-hydroxyethoxy)ethyl, is included.

As the sphingosine represented by general formula (2), one or two or more selected from a natural or natural-type sphingosine represented by the following general formula (3) and a derivative thereof (hereinafter, referred to as a natural-type sphingosine) or a pseudo sphingosine (hereinafter, referred to as a pseudo sphingosine) having a sphingosine structure represented by general formula (4) are preferable.

(I) Natural-type sphingosine represented by general formula (3).

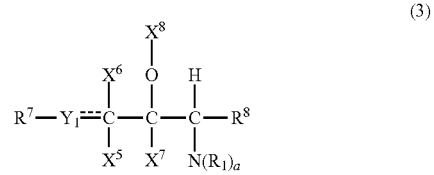

(3)

wherein $R^7$ represents a linear alkyl group having 7 to 24 carbon atoms, which is optionally substituted with a hydroxyl group; $Y_1$ represents a methylene group or a methine group; $X^5$, $X^6$ and $X^7$ each independently represent a hydrogen atom, a hydroxyl group or an acetoxy group; $X^8$ represents a hydrogen atom or forms an oxo group together with the adjacent oxygen atom, with the proviso that when $Y_1$ is a methine group, either one of $X^5$ and $X^6$ represents a hydrogen atom and the other is not present, and when $X^8$ forms an oxo group, $X^7$ is not present; $R^8$ represents a hydroxymethyl group or an acetoxymethyl group; each of $(R_1)_a$ independently represents a hydrogen atom or an amidino group or represents a linear alkyl group having 1 to 4 carbon atoms in total which optionally has a substituent selected from the group consisting of a hydroxyl group, a hydroxyalkoxy group, an alkoxy group and an acetoxy group; symbol a represents an integer of 2 or 3; and the broken line indicates that the bond may be an unsaturated bond.

Herein as $R^7$, a linear alkyl group having 7 to 24 carbon atoms is preferable and further a linear alkyl group having 13 to 24 carbon atoms is preferable. Symbol a preferably represents 2, each of $(R_1)_a$ preferably independently represents a hydrogen atom or a linear alkyl group having 1 to 4 carbon atoms.

As the natural-type sphingosine represented by general formula (3), one or two or more selected from the group consisting of natural sphingosine, dihydrosphingosine, phytosphingosine, sphingadienine, dehydrosphingosine, dehydrophytosphingosine and N-alkyl forms of these (for example, N-methyl form) are preferable.

As these sphingosines, a natural-type (D (+) form) optically active form, a non-natural-type (L (−) form) optically active form, and further a mixture of a natural-type and a non-natural-type may be used. As the relative configurations of the aforementioned compounds, not only natural-type configurations but also non-natural-type configurations as well as a mixture of these may be used.

Furthermore, one or two or more selected from PHYTOSPHINGOSINE (INCI name; 8th Edition) and the compounds represented by the following formulas are preferable.

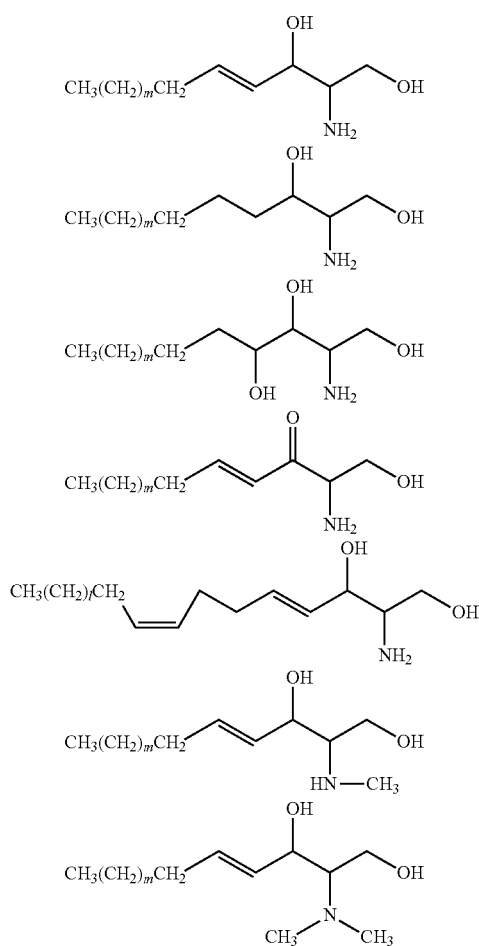

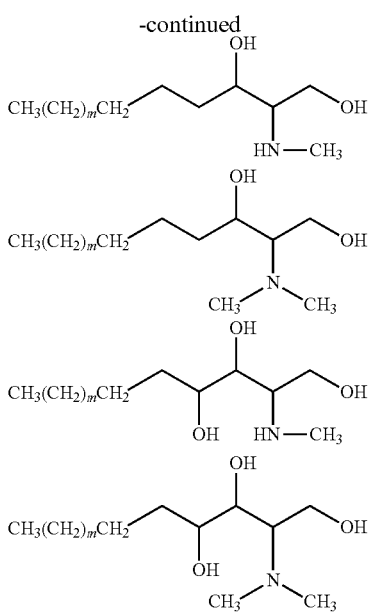

(wherein m represents 5 to 17 and l represents 1 to 13)

These may be either natural extracts or synthetic products and commercially available products can be used.

Examples of commercially available natural-type sphingosine include D-Sphingosine (4-Sphingenine) (Sigma-Aldrich Co. LLC.), DS-phytosphingosine (Doosan Corp.), and phytosphingosine (COSMOFERM).

(II) Pseudo sphingosine represented by general formula (4).

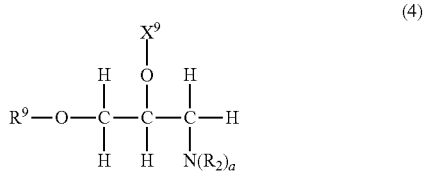

(4)

wherein $R^9$ represents a linear, branched or cyclic, and saturated or unsaturated hydrocarbon group having 10 to 22 carbon atoms, which is optionally substituted with a hydroxyl group; $X^9$ represents a hydrogen atom, an acetyl group or a glyceryl group; each of $(R_2)_a$ independently represents a hydrogen atom or an amidino group, or represents a linear or branched, and saturated or unsaturated hydrocarbon group having 1 to 8 carbon atoms in total, which optionally has a substituent selected from the group consisting of a hydroxyl group, a hydroxyalkoxy group, an alkoxy group and an acetoxy group; and symbol a represents an integer of 2 or 3.

Herein, as $R^9$, an iso-branched alkyl group having 14 to 20 carbon atoms is preferable and an isostearyl group is more preferable. As the isostearyl group, an isostearyl group obtained from isostearyl alcohol (as starting oil), which is derived from a by-product provided in producing a dimer acid using an animal/plant oil-derived fatty acid, is more preferable.

Furthermore, when symbol a is 2, $R_2$ represents $R_{21}$ and $R_{22}$, whereas when symbol a is 3, $R_2$ represents $R_{21}$, $R_{22}$ and $R_{23}$.

Examples of $R_{21}$, $R_{22}$ and $R_{23}$ include a hydrogen atom; linear or branched alkyl groups such as methyl, ethyl, propyl, 2-ethylhexyl and isopropyl; alkenyl groups such as vinyl and allyl; an amidino group; and an alkyl group having 1 to 8 carbon atoms in total and having a substituent selected from the group consisting of a hydroxyl group, a hydroxyalkoxy group and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl and 1,1-bis(hydroxymethyl)-2-hydroxyethyl.

Among them, preferable is a secondary amine wherein either one of $R_{21}$ and $R_{22}$ is a hydrogen atom and the other is 2-hydroxyethyl, 1,1-dimethyl-2-hydroxyethyl, 1,1-bis(hydroxymethyl)ethyl or 2-(2-hydroxyethoxy)ethyl.

As the pseudo sphingosine, sphingosine wherein $R^9$ is an isostearyl group, $X^9$ is a hydrogen atom, $R_{21}$ is a hydrogen atom and $R_{22}$ is an alkyl group having 1 to 3 substituents selected from the group consisting of a hydroxyl group and hydroxyalkoxy group, such as 2-hydroxyethyl group, a 1,1-bis(hydroxymethyl)ethyl group, a 1,1-dimethyl-2-hydroxyethyl group or 2-(2-hydroxyethoxy)ethyl group, is preferable.

As specific examples of the pseudo sphingosine, one or two or more selected from the following pseudo sphingosines (i) to (iv) are preferable.

Component (B) (one or more may be used) is contained in an amount of 0.0001 to 10 mass % in the total composition, preferably 0.001 to 5 mass % and more preferably 0.01 to 2 mass %. When the content falls within the range, a vesicle composition can be obtained without impairing sense of use.

In the present invention, the mass ratio of component (A) and component (B), (A)/(B), is preferably 0.001 or more and 50 or less in view of improving stability and adaptability to the skin upon application of the composition. The mass ratio is preferably 0.05 or more, more preferably 0.1 or more, further preferably 0.5 or more, and even more preferably 30 or less. When the vesicle composition of the present invention has a pH of 5.5 or more, the mass ratio of component (A) and component (B), (A)/(B), is more preferably 0.05 or more and 20 or less and further preferably 15 or less.

In the present invention, water as component (C) is preferably contained in an amount of 10 to 99 mass % and more preferably in an amount of 35 to 98 mass % in the total composition.

The vesicle composition of the present invention may further comprise (D) a ceramide. The ceramide is preferably contained because stability is improved.

As a ceramide, either a natural-type ceramide or a pseudo ceramide may be used and one or two or more selected from those represented by the following general formula (5) or (6) are preferable.

(I) Natural-type ceramide represented by general formula (5) may be a naturally-derived ceramide or a synthetic product having the same structure as the naturally-derived ceramide.

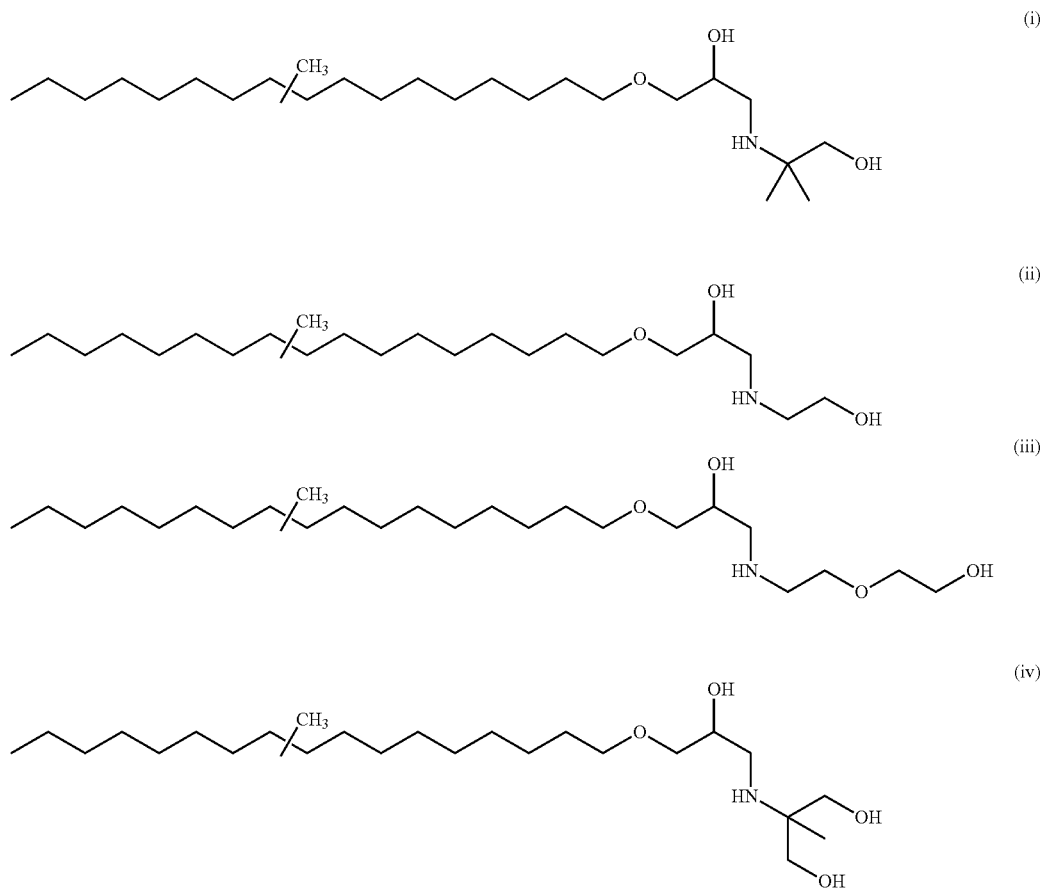

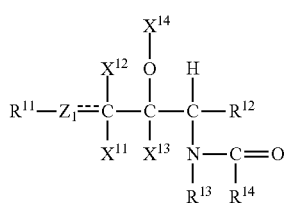

(5)

wherein $R^{11}$ represents a linear, branched or cyclic, and saturated or unsaturated hydrocarbon group having 7 to 19 carbon atoms which is optionally substituted with a hydroxyl group; $Z_1$ represents a methylene group or a methine group; $X^{11}$, $X^{12}$ and $X^{13}$ each independently represent a hydrogen atom, a hydroxyl group or an acetoxy group; $X^{14}$ represents a hydrogen atom or forms an oxo group together with the adjacent oxygen atom, with the proviso that when $Z_1$ is a methine group, either $X^{11}$ or $X^{12}$ is a hydrogen atom and the other is not present, and when $X^{14}$ forms an oxo group, $X^{13}$ is not present; $R^{12}$ represents a hydroxymethyl group or an acetoxymethyl group; $R^{13}$ represents a hydrogen atom or an alkyl group having 1 to 4 carbon atoms; $R^{14}$ represents a linear, branched or cyclic, and saturated or unsaturated hydrocarbon group having 5 to 30 carbon atoms, which is optionally substituted with a hydroxyl group, or represents a substituent in which a linear or branched, and saturated or unsaturated fatty acid having 8 to 22 carbon atoms which is optionally substituted with a hydroxyl group is ester-bonded to the ω terminal of the alkyl group; and the broken line indicates that the bond may be an unsaturated bond.

A compound wherein $R^{11}$ is a linear alkyl group having preferably 7 to 19 carbon atoms and further preferably 13 to 15 carbon atoms; and $R^{14}$ is a linear alkyl group having 9 to 27 carbon atoms, which is optionally substituted with a hydroxyl group, or a linear alkyl group having 9 to 27 carbon atoms, to which linoleic acid is bonded via ester bonding, is mentioned. Furthermore, it is preferable that $X^{14}$ represents a hydrogen atom or forms an oxo group together with an oxygen atom. In particular, as $R^{14}$, tricosyl, 1-hydroxypentadecyl, 1-hydroxytricosyl, heptadecyl, 1-hydroxyundecyl and a nonacocyl group to which linoleic acid is bonded at the ω position via ester bonding are preferable.

The natural type ceramide is preferably one or two or more selected from ceramide Types 1 to 7 in which sphingosine, dihydrosphingosine, phytosphingosine, or sphingadienine is amidated (for example, ceramides of pig and human described in FIG. 2 of J. Lipid Res., 24: 759 (1983), and FIG. 4 of J. Lipid. Res., 35: 2069 (1994)).

Furthermore, N-alkyl forms (for example, N-methyl form) of these are also included.

As these ceramides, a natural-type-type (D (−) form) optically active form, a non-natural (L (+) form) optically active form, and further a mixture of a natural-type and a non-natural-type may be used. The relative configuration of the above-mentioned compound may be configuration of a natural type, and configuration of the other non-natural type, and further a configuration of a mixture thereof. Among them, one or two or more compounds selected from CERAMIDE1, CERAMIDE2, CERAMIDE3, CERAMIDE5, CERAMIDE6II (all described in INCI, 8th Edition) and the compounds represented by the following formulas are preferable.

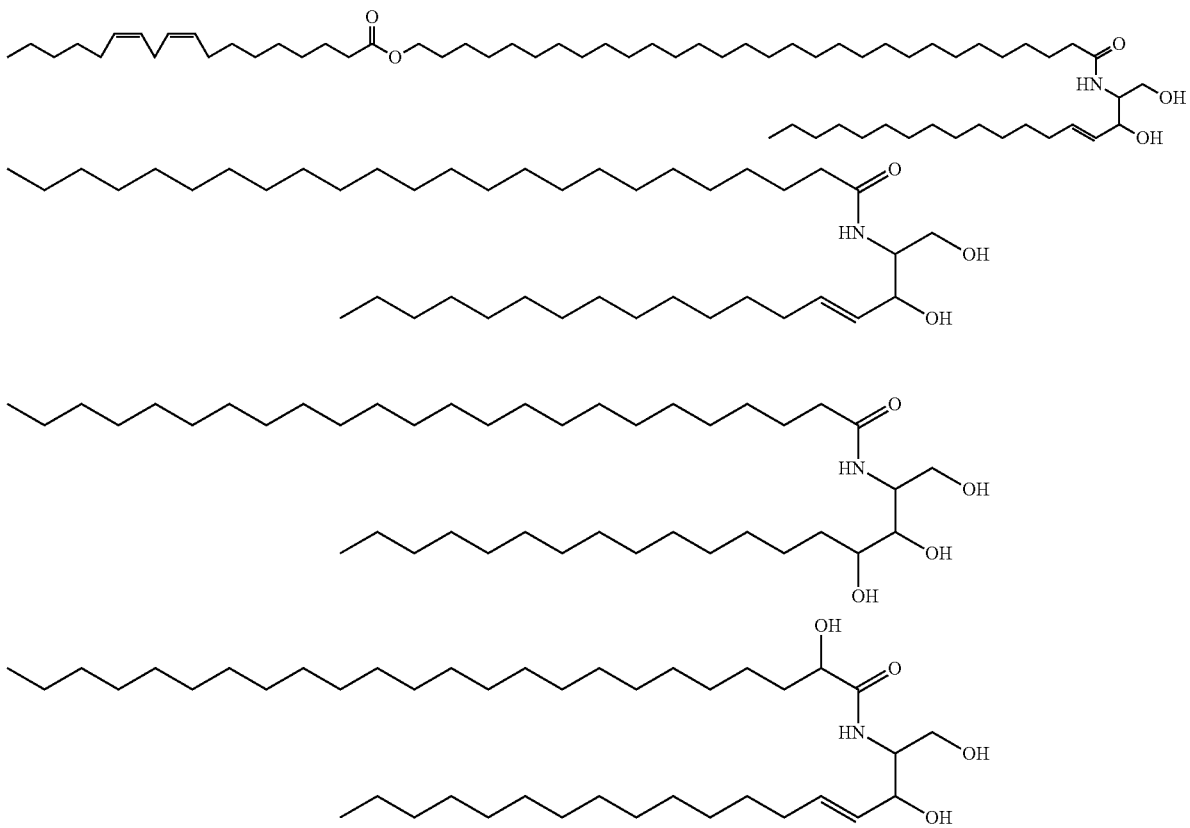

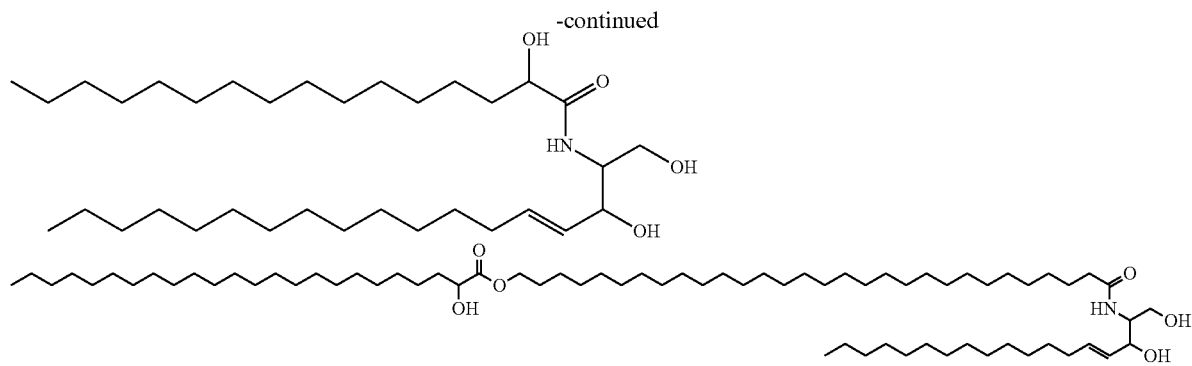

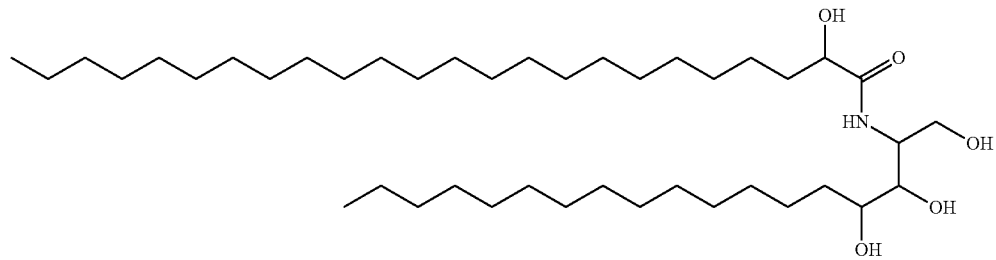 [SMILES: CCCCCCCCCCCCCCCCCCCCCCC(O)C(=O)NC(CO)C(O)C(O)CCCCCCCCCCCCCC]

These may be either natural extracts or synthetic products and commercially available products can be used.

If a commercially available product of a natural-type ceramide as mentioned above is used, one or two or more selected from Ceramide I, Ceramide III, Ceramide IIIA, Ceramide IIIB, Ceramide IIIC, Ceramide VI (all provided by COSMOFERM), Ceramide TIC-001 (Takasago International Corporation), CERAMIDE II (Quest International, Inc.), DS-Ceramide VI, DS-CLA-Phytoceramide, C6-Phytoceramide, DS-ceramide Y3S (Doosan Corp.), CERAMIDE2 (SEDAMA) are preferable.

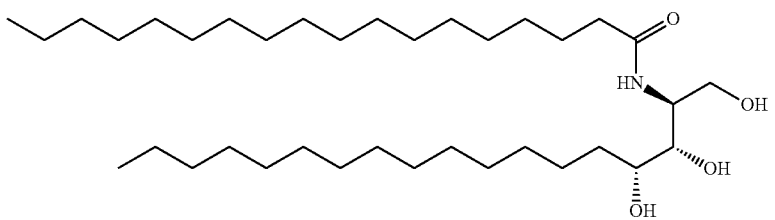

Ceramide III (COSMOFERM)

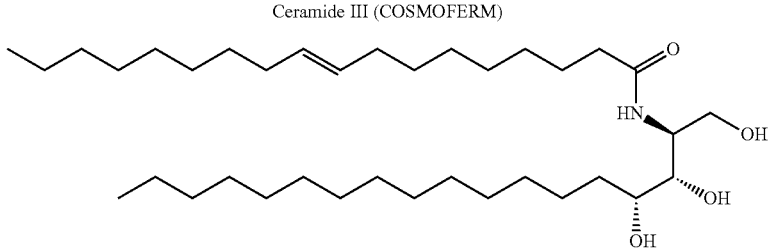

Ceramide IIIB (COSMOFERM)

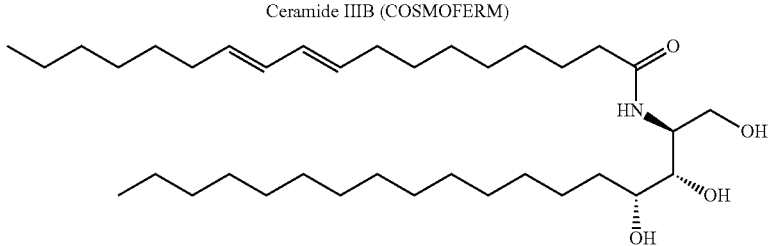

Ceramide IIIA (COSMOFERM)

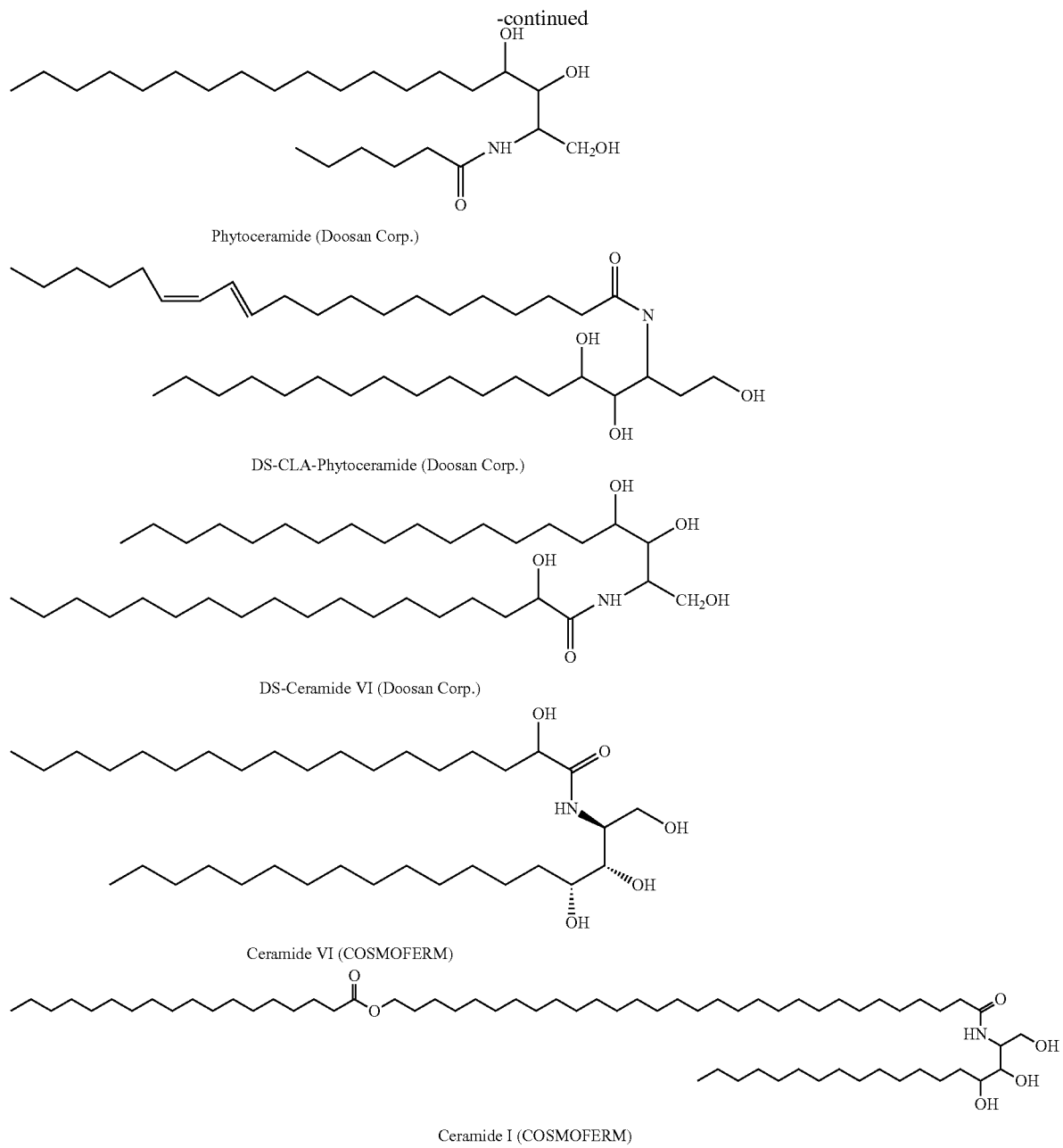

Phytoceramide (Doosan Corp.)

DS-CLA-Phytoceramide (Doosan Corp.)

DS-Ceramide VI (Doosan Corp.)

Ceramide VI (COSMOFERM)

Ceramide I (COSMOFERM)

(II) Pseudo ceramide represented by general formula (6).

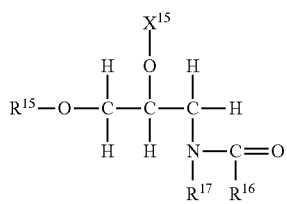

wherein $R^{15}$ represents a linear, branched or cyclic, and saturated or unsaturated hydrocarbon group having 10 to 22 carbon atoms, which is optionally substituted with a hydroxyl group, or represents a hydrogen atom; $X^{15}$ represents a hydrogen atom, an acetyl group or a glyceryl group; $R^{16}$ represents a linear, branched or cyclic, and saturated or unsaturated hydrocarbon group having 5 to 22 carbon atoms, which is optionally substituted with a hydroxyl group or an amino group, or represents a substituent in which a linear or branched, and saturated or unsaturated fatty acid having 8 to 22 carbon atoms which is optionally substituted with a hydroxyl group is ester-bonded to the ω terminal of the alkyl group; and $R^{17}$ represents a hydrogen atom or an alkyl group having 1 to 30 carbon atoms in total which is optionally substituted with a hydroxyl group, a hydroxyalkoxy group, an alkoxy group or an acetoxy group.

As $R^{16}$, in particular, nonyl, tridecyl, pentadecyl, an undecyl group to which a linoleic acid is bonded at the ω position via ester bonding, a pentadecyl group to which a linoleic acid is bonded at the ω position via ester bonding, a pentadecyl group to which a 12-hydroxystearic acid is bonded at the ω position via ester bonding, and an undecyl group to which a methyl branched isostearic acid is bonded at the ω position via amido bonding are preferable.

$R^{17}$ is an alkyl group having 10 to 30 carbon atoms in total, preferably 12 to 20 carbon atoms in total which is optionally substituted with a hydroxyl group, a hydroxyalkoxy group, an alkoxy group or an acetoxy group, if $R^{15}$ is a hydrogen atom. If $R^{15}$ is a linear, branched or cyclic, and saturated or unsaturated hydrocarbon group having 10 to 22 carbon atoms, which is optionally substituted with a hydroxyl group, $R^{17}$ represents preferably a hydrogen atom or represents an alkyl group having 1 to 8 carbon atoms in total, which is optionally substituted with a hydroxyl group, a hydroxyalkoxy group, an alkoxy group or an acetoxy group. As the hydroxyalkoxy group or alkoxy group represented by $R^{17}$, those having 1 to 7 carbon atoms are preferable.

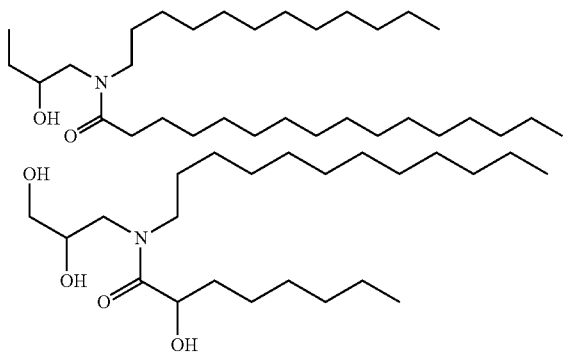

As the pseudo ceramide represented by general formula (6), one or more pseudo ceramides selected from the compound wherein $R^{15}$ is a hexadecyl group, $X^{15}$ is a hydrogen atom, $R^{16}$ is a pentadecyl group and $R^{17}$ is a hydroxyethyl group; and the compound wherein $R^{15}$ is a hexadecyl group, $X^{15}$ is a hydrogen atom, $R^{16}$ is a nonyl group and $R^{17}$ is a hydroxyethyl group are preferable; and N-(hexadecyloxy-hydroxypropyl)-N-hydroxyethylhexadecanamide represented by general formula (6) wherein $R^{15}$ is a hexadecyl group, $X^{15}$ is a hydrogen atom, $R^{16}$ is a pentadecyl group and $R^{17}$ is a hydroxyethyl group is further preferable.

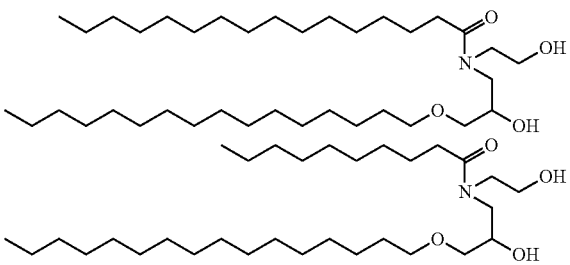

A ceramide as component (D), if it is mixed with components (A), (B) and (C), stabilizes a vesicle structure formed of components (A) and (B) and contributes to storage stability. Furthermore, a ceramide as component (D), if it is contained in a vesicle structure formed of components (A) and (B), suppresses crystallization and contributes to stabilization.

A ceramide as component (D) (one or more may be used) is preferably contained in an amount of 0.0001 to 50 mass %, more preferably 0.001 to 25 mass % and further preferably 0.01 to 10 mass % in the total composition.

In the present invention, the mass ratio of component (D) and component (B), (B)/(D), is preferably 0.01 to 15, more preferably 0.05 to 10 and further preferably 0.05 to 5 in view of further improving stability and adaptability of water to the skin and enhancing water retention amount on the skin after use.

The vesicle composition of the present invention may further comprise (E) cholesterol or a derivative thereof. This is preferable since stability is more improved.

As the cholesterol derivative, a fatty acid cholesterol ester is mentioned and a cholesterol ester of a fatty acid having 12 to 24 carbon atoms is preferable. More specifically, one or two or more selected from the group consisting of cholesteryl laurate, cholesteryl palmitate, cholesteryl myristate, cholesteryl oleate, cholesteryl isostearate and cholesteryl linoleate are preferable.

Cholesterol or a derivative thereof as component (E), if it is mixed with components (A), (B) and (C), stabilizes a vesicle structure formed of components (A) and (B) and contributes storage stability.

Cholesterol or a derivative thereof (one or more may be used) is preferably contained in an amount of 0.0001 to 10 mass %, more preferably 0.001 to 5 mass % and further preferably 0.01 to 3 mass % in the total composition in view of further improving sense of use.

The vesicle composition of the present invention may further comprise (F) a fatty acid. This is preferable since stability is improved. The fatty acid as component (F) is soluble in oil and differs from acids of component (A) and component (H) described later, which provide acidic pH if dissolved in water.

As the fatty acid, those having a hydrocarbon group of 8 to 30 carbon atoms and further 12 to 30 carbon atoms are preferable. For example, one or two or more selected from the group consisting of isostearic acid, oleic acid, myristic acid, palmitic acid, stearic acid, arachic acid, behenic acid, lignoceric acid, cerotic acid, montanic acid and melissic acid are preferable.

A fatty acid is preferably contained in an amount of 0.0001 to 10 mass %, more preferably 0.001 to 5 mass % and further preferably 0.01 to 3 mass % in the total composition in view of improving adaptability upon application.

The composition of the present invention may further comprise (G) a base other than component (B) and/or (H) an acid other than component (A) for controlling pH.

The base as component (G) is not particularly limited and may be an organic base or an inorganic base.

The organic base is preferably one or two or more selected from basic amino acids and alkanol amines. Specifically, one or two or more selected from basic amino acids such as L-arginine, lysine and histidine; and alkanol amines such as monoethanolamine, diethanolamine, triethanolamine, aminomethyl propanol, aminomethyl propanediol, aminoethyl propanediol and trishydroxymethyl amino ethane are preferable.

Furthermore, the inorganic base is preferably one or two or more selected from the group consisting of calcium hydroxide, sodium hydroxide and potassium hydroxide.

Among them, one or two or more selected from the group consisting of L-arginine, calcium hydroxide, sodium hydroxide and potassium hydroxide are more preferable.

The base as component (G) (one or two or more may be used in combination) is preferably contained in an amount of 0 to 10 mass and further preferably in an amount of 0.001 to 5 mass % in the total composition in view of further improving sense of use.

Furthermore, as the acid as component (H), either an organic acid or an inorganic acid may be used as long as it is an acid other than component (A).

The organic acid is preferably one or two or more selected from the group consisting of a monocarboxylic acid, a dicarboxylic acid, an oxycarboxylic acid and an acidic amino acid. More specifically, one or two or more selected from monocarboxylic acids such as acetic acid, propionic acid and butyric acid; dicarboxylic acids such as succinic acid, phthalic acid, fumaric acid, oxalic acid, malonic acid and glutaric acid; oxycarboxylic acids such as glycolic acid, citric acid, lactic acid, pyruvic acid, malic acid and tartaric acid; and acidic amino acids such as glutaminic acid and aspartic acid are preferable.

Furthermore, the inorganic acid is preferably one or two or more selected from hydrochloric acid, nitric acid, nitrous acid, sulfuric acid, sulfurous acid, phosphoric acid, phosphonic acid and phosphinic acid.

Among them, one or two or more selected from an acidic amino acid and phosphoric acid, are preferable.

Component (H) (one or more may be used) is preferably contained in an amount of 0 to 10 mass % and more preferably 0.001 to 5 mass % in the total composition.

A method for producing a vesicle composition of the present invention comprises Step 1 of mixing an oil phase comprising component (A) and (B) with heating, and Step 2 of mixing component (C) comprising a water soluble component and stirring.

It is preferable that after Step 1, Step 12 of dissolving component (G) or component (H) in part of component (C) and adding the solution to the oil phase and mixing them, and Step 13 of cooling the mixture after Step 12 are provided. Furthermore, after Step 2, Step 22 of dissolving component (G) or component (H) in part of component (C) and adding the solution to the composition and mixing them can be provided. Note that, in these cases, the content of component (C) is defined as the sum of the amounts mixed in individual steps. Furthermore, in the step of mixing components with heating, the heating temperature is preferably the highest temperature of the melting points of components to be mixed or more and 100° C. or less.

The method for producing a vesicle composition of the present invention preferably comprises Step 1 of mixing an oil phase comprising components (A) and (B) with heating, Step 12 of dissolving component (G) or component (H) in part of component (C), adding the solution to the oil phase and mixing them, Step 13 of cooling the mixture after Step 12 and Step 2 of mixing a water phase comprising the remaining component (C) and stirring the mixture.

Furthermore, according to the method for producing a vesicle composition of the present invention, in Step 12, after Step 1 of mixing an oil phase comprising components (A) and (B), component (H) is dissolved in part of component (C), added to the oil phase and mixed to successfully control pH to preferably 5.5 or less and more preferably 5 or less. Furthermore, in Step 22, component (G) is dissolved in part of component (C) and added to the composition to successfully control pH to 2 to 11.

Alternatively, in Step 12, after Step 1 of mixing an oil phase comprising components (A) and (B), component (G) is dissolved in part of component (C), added to the oil phase and mixed to successfully control pH to be preferably larger than 5.5 and more preferably 7 or more. Furthermore, in Step 22, component (H) is dissolved in part of component (C) and added to the composition to successfully control pH to 2 to 11.

According to the method for producing a vesicle composition of the present invention, it is preferable that Step 12 is a step of controlling pH to be larger than 5.5 and more preferably 7 or more by dissolving component (G) in part of component (C) and adding the solution to an oil phase and mixing them; and after Step 2, Step 22 of dissolving component (H) in part of component (C) and adding the solution to the composition to control pH to 2 to 11 is provided.

Furthermore, it is preferable that Step 12 is a step of controlling pH to be 5.5 or less by dissolving component (H) in part of component (C), adding the solution to an oil phase and mixing them; and after Step 2, pH is controlled to 2 to 11 by dissolving component (G) in part of component (C) and adding the solution to the composition.

Component (H), which is an acid other than component (A), serves to shift the system to an acidic condition and cationizes component (B). As a result, in the acidic condition, component (B) serves as a surfactant and component (A) serves as a co-surfactant to successfully form a vesicle structure.

In contrast, component (G), which is a base other than component (B), serves to shift the system to a basic condition and anionizes component (A). As a result, in the basic conditions, component (A) serves as a surfactant, component (B) serves as a co-surfactant to successfully form a vesicle structure.

Therefore, in the present invention, a stable vesicle structure can be formed in both of acidic and basic conditions.

The vesicle composition of the present invention has a pH of 2 to 11. In view of reducing stimulus to the skin and sense of use, pH is preferably 3 to 9.5 and more preferably 4 to 8. In view of further improving stability, the pH of a vesicle composition is preferably 3 or more and less than 5.5 or larger than 5.5 and 9.5 or less and more preferably 3 or more and 5.2 or less or 6 or more and 8 or less.

Note that, in the present invention, pH is measured by a pH meter at 25° C.

In the present invention, formation of a vesicle can be confirmed by observing Maltese Cross under a microscope (polarization).

A vesicle is susceptible to salt and thus a water soluble polymer is preferably comprised in the composition.

As a water soluble polymer, a water soluble polymer having an alkyl group, in particular, an alkyl group having 8 to 30 carbon atoms, is preferable, and a polymer of (meth)acrylic acid having an alkyl group or a polymer having a sugar skeleton is further preferable.

More specifically, one or two or more selected from the group consisting of alkyl-modified carboxyvinyl polymers such as an acrylic acid-alkyl methacrylate copolymer; alkyl acrylate-alkyl methacrylate-polyoxyethylene (20) stearyl ether copolymers; alkyl modified cellulose derivatives described in JP-A-9-87130; polysaccharide derivatives such as sodium hydroxyethylcellulose hydroxypropyl stearyl ether hydroxypropylsulfonate described in JP-A-9-235301 and JP-A-10-292001; and polysaccharide derivatives described in JP-A-2006-117746 are preferable.

It is preferable that such a water soluble polymer (one or more may be used) is contained in an amount of 0.0001 to 10 mass % and more preferably in an amount of 0.01 to 5 mass % in the total composition.

The vesicle composition of the present invention may be applied as a skin preparation for external application, cosmetics and others.

If applied as a cosmetic product, the vesicle composition may further comprise, in addition to the aforementioned components, components usually used in cosmetics, for example, oily components, lower alcohols, moisturizers, antioxidants, preservatives, chelating agents, whitening agents, UV-absorbers, vitamins, plant extracts, other medicinal ingredients, powders, perfumes and colorants. Furthermore, regarding the above mentioned embodiment, the present invention also includes other embodiments described below, related to the composition, the method for producing the composition, and use of the composition.

[1] A vesicle composition comprising the following components (A), (B) and (C):

(A) 0.0001 to 20 mass % of an organic acid represented by general formula (1):

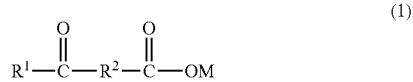

wherein $R^1$ represents a natural sterin having a single hydroxy group or a hydrogenated product thereof or a residue which remains after a hydrogen atom is removed from the hydroxy group of bile acid, $R^2$ represents a divalent hydrocarbon group having 1 to 24 carbon atoms, M represents a hydrogen atom, an alkali metal, an alkali earth metal, ammonium, an alkanolammonium having 2 to 9 carbon atoms in total, an alkylammonium or alkenylammonium having 1 to 22 carbon atoms in total, pyridinium substituted with an alkyl group or alkenyl group having 1 to 18 carbon atoms or a basic amino acid, (B) 0.0001 to 10 mass % of a sphingosine, and (C) water, and having a pH of 2 to 11.

[2] The vesicle composition according to item [1], further comprising (D) a ceramide.

[3] The vesicle composition according to item [2], wherein the component (D) comprises one or two or more selected from a natural-type ceramide and a pseudo ceramide, preferably one or two or more selected from a natural-type ceramide represented by general formula (5):

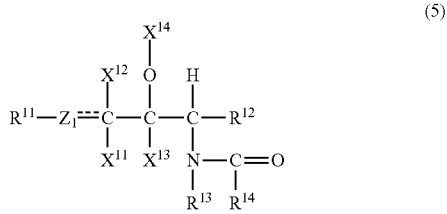

wherein $R^{11}$ represents a linear, branched or cyclic, and saturated or unsaturated hydrocarbon group having 7 to 19 carbon atoms, which is optionally substituted with a hydroxyl group; $Z_1$ represents a methylene group or a methine group; $X^{11}$, $X^{12}$ and $X^{13}$ each independently represent a hydrogen atom, a hydroxyl group or an acetoxy group; $X^{14}$ represents a hydrogen atom or forms an oxo group together with the adjacent oxygen atom, with the proviso that when $Z_1$ is a methine group, either $X^{11}$ or $X^{12}$ is a hydrogen atom and the other is not present, and when $X^{14}$ forms an oxo group, $X^{13}$ is not present; $R^{12}$ represents a hydroxymethyl group or an acetoxymethyl group; $R^{13}$ represents a hydrogen atom or an alkyl group having 1 to 4 carbon atoms; $R^{14}$ represents a linear, branched or cyclic, and saturated or unsaturated hydrocarbon group having 5 to 30 carbon atoms, which is optionally substituted with a hydroxyl group, or represents a substituent in which a linear or branched, and saturated or unsaturated fatty acid having 8 to 22 carbon atoms which is optionally substituted with a hydroxyl group is ester-bonded to the ω terminal of the alkyl group; and the broken line indicates that the bond may be an unsaturated bond, and a pseudo ceramide represented by general formula (6):

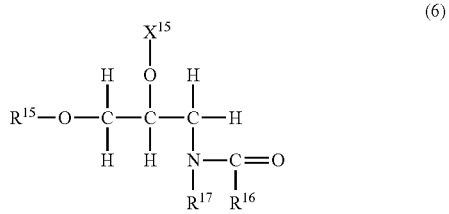

wherein $R^{15}$ represents a linear, branched or cyclic, and saturated or unsaturated hydrocarbon group having 10 to 22 carbon atoms, which is optionally substituted with a hydroxyl group or represents a hydrogen atom; $X^{15}$ represents a hydrogen atom, an acetyl group or a glyceryl group; $R^{16}$ represents a linear, branched or cyclic, and saturated or unsaturated hydrocarbon group having 5 to 22 carbon atoms, which is optionally substituted with a hydroxyl group or an amino group, or represents a substituent in which a linear or branched, and saturated or unsaturated fatty acid having 8 to 22 carbon atoms which is optionally substituted with a hydroxyl group is ester-bonded to the ω terminal of the hydrocarbon group; and $R^{17}$ represents a hydrogen atom or represents an alkyl group having 1 to 30 carbon atoms in total, which is optionally substituted with a hydroxyl group, a hydroxyalkoxy group, an alkoxy group or an acetoxy group.

[4] The vesicle composition according to item [2] or [3], wherein the content of component (D) is 0.0001 to 50 mass %, preferably 0.001 to 25 mass % and more preferably 0.01 to 10 mass %.

[5] The vesicle composition according to any one of items [1] to [4], further comprising (E) cholesterol or a derivative thereof.

[6] The vesicle composition according to item [5], wherein the content of component (E) is 0.0001 to 10 mass %, preferably 0.001 to 5 mass % and more preferably 0.01 to 3 mass %.

[7] The vesicle composition according to item [5] or [6], wherein component (E) is cholesterol or a fatty acid cholesterol ester, preferably cholesterol or a fatty acid cholesterol ester having 12 to 24 carbon atoms, and more preferably, one or two or more selected from the group consisting of cholesterol, cholesteryl laurate, cholesteryl palmitate, cholesteryl myristate, cholesteryl oleate, cholesteryl isostearate and cholesteryl linoleate.

[8] The vesicle composition according to any one of items [1] to [7], further comprising (F) a fatty acid.

[9] The vesicle composition according to item [8], wherein the content of component (F) is 0.0001 to 10 mass %, preferably 0.001 to 5 mass % and more preferably 0.01 to 3 mass %.

[10] The vesicle composition according to item [8] or [9], wherein the fatty acid (F) is the compound with a hydrocarbon group having 8 to 30 carbon atoms, preferably a hydrocarbon group having 12 to 30 carbon atoms, and more preferably one or two or more fatty acids selected from the group consisting of isostearic acid, oleic acid, myristic acid, palmitic acid, stearic acid, arachic acid, behenic acid, lignoceric acid, cerotic acid, montanic acid and melissic acid.

[11] The vesicle composition according to any one of items [1] to [10], further comprising at least one selected from (G) a base other than component (B) and (H) an acid other than component (A).

[12] The vesicle composition according to any one of items [1] to [11], wherein component (B) comprises at least one represented by general formula (2):

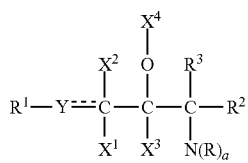

(2)

wherein $R^1$ represents a linear alkyl group having 4 to 30 carbon atoms, which is optionally substituted with a hydroxyl group, carbonyl group or amino group; Y represents a methylene group, a methine group or an oxygen atom; $X^1$, $X^2$, and $X^3$ each independently represent a hydrogen atom, a hydroxyl group or an acetoxy group; $X^4$ represents a hydrogen atom, an acetyl group or a glyceryl group or forms an oxo group together with the adjacent oxygen atom, with the proviso that when Y is a methine group, either $X^1$ or $X^2$ is a hydrogen atom and the other is not present, and when $X^4$ forms an oxo group, $X^3$ is not present; $R^2$ and $R^3$ each independently represent a hydrogen atom, a hydroxyl group, a hydroxymethyl group or an acetoxymethyl group; symbol a represents an integer of 2 or 3; each of $(R)_a$ independently represents a hydrogen atom or an amidino group, or represents a linear alkyl group having 1 to 8 carbon atoms in total, which optionally has a substituent selected from the group consisting of a hydroxyl group, a hydroxyalkoxy group, an alkoxy group and an acetoxy group; and the broken line indicates that the bond may be an unsaturated bond, and preferably comprises at least one selected from the group consisting of natural-type sphingosine and pseudo sphingosine, and more preferably, at least one selected from the group consisting of natural sphingosine, dihydrosphingosine, phytosphingosine, sphingadienine, dehydrosphingosine and pseudo sphingosines selected from formulas (i) to (iv):

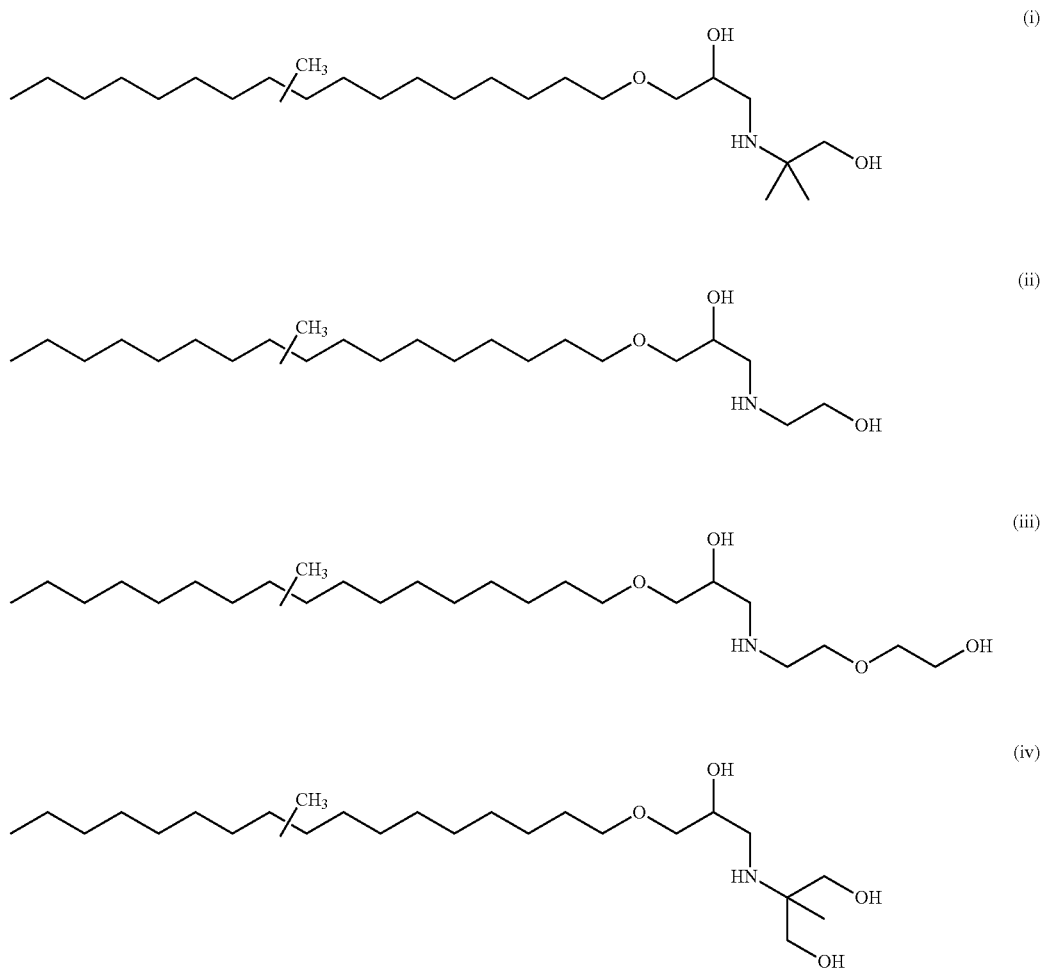

[13] The vesicle composition according to any one of items [1] to [12], wherein component (A) is represented by general formula (1) wherein $R^1$ is at least one selected from the group consisting of cholesterol, stigmasterol, sitosterol, campesterol, lanosterol and ergosterol and preferably cholesterol.

[14] The vesicle composition according to any one of items [1] to [13], wherein the content of component (A) is 0.001 to 15 mass % and preferably 0.01 to 10 mass %.

[15] The vesicle composition according to any one of items [1] to [14], wherein the content of component (B) is 0.001 to 5 mass % and preferably 0.01 to 2 mass %.

[16] The vesicle composition according to any one of items [1] to [15], being a cosmetic product.

[17] A method for producing the vesicle composition according to any one of items [1] to [16], wherein the method comprises the following steps:

Step 1 of mixing an oil phase comprising components (A) and (B) with heating;

Step 12 of dissolving (G) a base other than component (B) or (H) an acid other than component (A) in part of component (C), adding the solution to the oil phase and mixing them, Step 13 of cooling the mixture after the Step 12;

and Step 2 of mixing a water phase comprising the remaining component (C) and stirring.

[18] The method for producing the vesicle composition according to item [17], wherein the Step 12 is a step of controlling pH to be larger than 5.5 by dissolving component (G) in part of component (C) and adding the solution to the oil phase and mixing them, and after the Step 2, Step 22 of controlling pH to 2 to 11 by dissolving component (H) in part of component (C) and adding the solution to the composition is provided.

[19] The method for producing the vesicle composition according to item [18], wherein the Step 12 is a step of controlling pH to be 7 and more by dissolving component (G) in part of component (C) and adding the solution to the oil phase and mixing them.

[20] The method for producing the vesicle composition according to item [17], wherein the Step 12 is a step of controlling pH to be 5.5 or less by dissolving component (H) in part of component (C) and adding the solution to the oil phase and mixing them, and after the Step 2, Step 22 of controlling pH to 2 to 11 by dissolving component (G) in part of component (C) and adding the solution to the composition is provided.

[21] The method for producing the vesicle composition according to item [20], wherein the Step 12 is a step of controlling pH to be 5.5 or less by dissolving component (H) in part of component (C) and adding the solution to the oil phase and mixing them.

[22] Use of the vesicle composition according to any one of items [1] to [15], in the production of a skin preparation for external application.

[23] Use of the vesicle composition according to any one of items [1] to [15], in the production of a cosmetic product.

EXAMPLES

Examples 1 to 18, Comparative Examples 1 to 2

Compositions having formulations shown in Table 1 were produced and pH, state of vesicles, storage stability and adaptability upon application were evaluated. The results are shown together in Table 1.

(Production Method)

Component (G) or component (H) was separately dissolved in 15 mass % of water as component (C).

In Examples 1, 5, 7 to 9 and 12, components (A), (B), (D), (E), (F) and oily component(s) are mixed and dissolved while heating at 80° C. to 95° C. and stirred. Next, component (G) dissolved in part of water as component (C) was added and homogenized. Thereafter, the mixture was cooled to 25° C. while stirring. Subsequently, polyol(s), other components and the remaining part of component (C) were mixed and homogenized with stirring.

In Examples 3, 6, 10 and 14, components (A), (B), (D), (E), (F) and oily component(s) are mixed and dissolved while heating at 80° C. to 95° C. and stirred. Further, component (H) dissolved in part of water as component (C) was added and homogenized. Thereafter, the mixture was cooled to 25° C. while stirring. Subsequently, polyol(s), other components and the remaining part of component (C) were mixed and homogenized with stirring.

In Examples 2 and 13, components (A), (B), (D) and (E) are mixed and dissolved while heating at 80° C. to 95° C. and stirred. Further, component (G) dissolved in part of water as component (C) was added and homogenized. Thereafter, the mixture was cooled to 25° C. while stirring. Subsequently, polyol(s), other components and the remaining part of component (C) excluding a part thereof were mixed and homogenized with stirring. Next, component (H) dissolved in the part of water as component (C) was added and homogenized (stability of vesicles by pH change was checked).

In Examples 4, 15 and 18, components (A), (B), (D) and (E) are mixed and dissolved while heating at 80° C. to 95° C. and stirred. Further, component (H) dissolved in part of water as component (C) was added and homogenized. Thereafter, the mixture was cooled to 25° C. while stirring. Next, polyol(s), other components and the remaining part of component (C) excluding a part thereof were mixed and homogenized with stirring. Further, component (G) dissolved in the part of water as component (C) was added and homogenized (stability of vesicles by pH change was checked).

In Example 11, individual components are mixed and dissolved while heating at 80° C. to 95° C. and stirred. Thereafter, the mixture was cooled to 25° C. while stirring.

In Example 16, components (A), (B), (D), (E) and (F) are mixed and dissolved while heating at 80° C. to 95° C. and stirred. Further, component (H) dissolved in part of water as component (C) was added and homogenized. Thereafter, the mixture was cooled to 25° C. while stirring. Subsequently, the remaining part of component (C) excluding a part thereof was mixed and homogenized with stirring. Further, component (G) dissolved in the part of water as component (C) was added and homogenized (stability of vesicles by pH change was checked).

In Example 17, components (A), (B), (D), (E) and (F) are mixed and dissolved while heating at 80° C. to 95° C. and stirred. Further, component (G) dissolved in part of water as component (C) was added and homogenized. Thereafter, the mixture was cooled to 25° C. while stirring. Subsequently, the remaining part of component (C) excluding a part thereof was mixed and homogenized with stirring. Further, component (H) dissolved in the part of water as component (C) was added and homogenized (stability of vesicles by pH change was checked).

In Comparative Example 1, components (A), (D) and (E) are mixed and dissolved while heating at 80° C. to 95° C. and stirred. Further, component (G) dissolved in part of water as component (C) was added and homogenized.

Thereafter, the mixture was cooled to 25° C. while stirring. Subsequently, polyol(s) and the remaining part of component (C) excluding a part thereof were mixed and homogenized with stirring. Further, component (H) dissolved in the part of water as component (C) was added and homogenized (stability of vesicles by pH change was checked).

In Comparative Example 2, components (B), (D) and (E) are mixed and dissolved while heating at 80° C. to 95° C. and stirred. Further, component (H) dissolved in part of water as component (C) was added and homogenized. Thereafter, the mixture was cooled to 25° C. while stirring. Subsequently, polyol(s) and the remaining part of component (C) excluding a part thereof were mixed and homogenized with stirring. Further, component (G) dissolved in the part of water as component (C) was added and homogenized (stability of vesicles by pH change was checked).

(Evaluation Method)

(1) pH:

Measurement was performed by COMPACT pH METER B-212 manufactured by HORIBA, Ltd. at 25° C.

Note that, in Examples 1, 3, 5 to 12 and 14, pH was measured immediately after individual components were mixed and prepared. Furthermore, in Examples 2, 4, 13 and 15 to 18, pH was measured before and after mixing component (G) or (H) to be finally mixed.

(2) State of Vesicle:

In Examples 1, 3, 5 to 12, and 14, vesicles were confirmed by observing Maltese Cross under a microscope (polarization) immediately after individual components were mixed and prepared. Furthermore, in Examples 2, 4, 13 and 15 to 18, vesicles were confirmed by observing Maltese Cross under a microscope (polarization) before and after mixing component (G) or (H) to be finally mixed. The case where Maltese Cross was observed was indicated by "A" and the case where Maltese Cross was not observed was indicated by "B".

(3) Storage Stability:

Individual compositions were stored separately at 50° C., 25° C. and 5° C. for a week and thereafter appearance was observed by the naked eye. In addition, the presence or absence of vesicles and precipitation of crystals were observed by an optical microscope. Note that, formation of vesicles was confirmed by observing Maltese Cross under a microscope.

The results were evaluated as follow. The case where precipitation of crystals and disappearance of vesicles were not observed and excellent stability was obtained was indicated by "A"; the case where precipitation of crystals and disappearance of vesicles were not observed, a slight change in appearance such as viscosity was observed was indicated by "B", and the case where precipitation of crystals or disappearance of vesicles was observed and stability was not obtained was indicated by "C".

(4) Adaptability Upon Application:

"Adaptability" was evaluated by a sensory test made by 10 expert panelists. Each of emulsion compositions (about 0.1 g) was applied to back of their hands and the results were indicated by the number of panelists who evaluated as "adaptable".

TABLE 1

| | Component (mass %) | Example | | | | | | | | | |
|---|---|---|---|---|---|---|---|---|---|---|---|
| | | 1 | 2 | 3 | 4 | 5 | 6 | 7 | 8 | 9 | 10 |
| A | n-Octadecenylsuccinic acid cholesteryl monoester | 1 | 1 | 1 | 1 | 1.25 | 1.25 | | | | |
| | n-Hexadecenylsuccinic acid cholesteryl monoester | | | | | | | | | | 1.5 |
| | Cholesterol hydrogen succinate (manufactured by Tokyo Chemical Industry Co., Ltd.) | | | | | | | 0.2 | 0.2 | 0.2 | |
| B | Phytosphingosine (manufactured by COSMOFERM) | 0.1 | 0.1 | 0.1 | 0.1 | | 0.05 | | | | |
| | Pseudo sphingosine (ii) | | | | | 0.1 | | 0.2 | 0.2 | 0.2 | 0.2 |
| G | L-arginine | 0.5 | 0.5 | | | | | 0.2 | 0.2 | 0.2 | |
| | Potassium hydroxide | | | | 0.3 | 0.017 | | | | | |
| H | L-glutamic acid | | | 0.06 | 0.06 | | 0.05 | | | | 0.45 |
| | Phosphoric acid | | 0.3 | 0.05 | 0.05 | | | | | | |
| D | N-(hexadecyloxyhydroxypropyl)-N-hydroxyethylhexadecanamide | | | | | 1 | 1 | 2 | 2 | 2 | 2 |
| | Ceramide (type 2) | 1 | 1 | 1 | 1 | | | | | | |
| E | Cholesterol | 0.5 | 0.5 | 0.5 | 0.5 | 0.25 | 0.25 | | 0.5 | 0.5 | 1.5 |
| | Cholesteryl isostearate | | | | | | 0.1 | | | | 1.5 |
| F | Stearic acid | | | | | | 0.1 | | 0.5 | | |
| | Squalane | | | | | 0.5 | 0.5 | | | | 16 |
| | Dimethylpolysiloxane | | | | | | 1 | | | | 3.25 |
| | Cetanol | | | | | | 0.2 | | | | |
| | 1,3-butylene glycol | | | | | 5 | 5 | | | | 5 |
| | Glycerin | 5 | 5 | 5 | 5 | 10 | 10 | | | | |
| | Carboxyvinyl polymer | | | | | | 0.1 | | | | 0.1 |
| | Hydroxyethyl(hydroxypropylpolyethyleneglycol dodecyl ether) cellulose | | | | | | 0.15 | | | | 0.8 |

TABLE 1-continued

|  | Component (mass %) | | | | | | | | | | |
|---|---|---|---|---|---|---|---|---|---|---|---|
|  | O-[2-hydroxy-3-(trimethylammonio)propyl]hydroxyethyl cellulose chloride | | | | | | 0.5 | | | | |
|  | Methyl paraoxybenzoate | | | | | 0.2 | 0.2 | | | | |
| C | Ion exchange water | Balance | Balance | Balance | Balance | Balance | Balance | Balance | Balance | Balance | Balance |
| Total | | 100 | 100 | 100 | 100 | 100 | 100 | 100 | 100 | 100 | 100 |
| pH: At the time of preparation | | 9.2 | 9.2 | 3.2 | 3.2 | 6.8 | 4.5 | 9.2 | 9.8 | 9.2 | 5.2 |
| After component (G) or (H) was added after preparation | | | 3.9 | | 8.1 | | | | | | |
| State of vesicle immediately after preparation | | A | A | A | A | A | A | A | A | A | A |
| State of vesicle after pH was changed immediately after preparation | | | A | | A | | | | | | |
| Storage stability: 50° C. | | A | A | A | A | A | A | A | A | A | A |
| 25° C. | | A | A | A | A | A | A | C | B | A | A |
| 5° C. | | A | A | A | A | A | A | A | A | A | A |
| Adaptability upon application (the number of panelists who evaluated as "adaptable") | | 7 | 8 | 7 | 7 | 7 | 9 | 8 | 8 | 9 | 7 |

|  |  | Example | | | | | | | | Comp. Ex. | |
|---|---|---|---|---|---|---|---|---|---|---|---|
|  | Component (mass %) | 11 | 12 | 13 | 14 | 15 | 16 | 17 | 18 | 1 | 2 |
| A | n-Octadecenylsuccinic acid cholesteryl monoester | | | | | | | | | 1 | |
|  | n-Hexadecenylsuccinic acid cholesteryl monoester | 2.15 | 1 | 1 | 1 | 1 | 7 | 7 | 0.05 | | |
|  | Cholesterol hydrogen succinate (manufactured by Tokyo Chemical Industry Co., Ltd.) | | | | | | | | | | |
| B | Phytosphingosine (manufactured by COSMOFERM) | | | | | | 1.5 | 1.5 | | | 0.1 |
|  | Pseudo sphingosine (ii) | 1.1 | 0.2 | 0.2 | 1.0 | 1.0 | | | 1 | | |
| G | L-arginine | | 0.5 | 0.5 | | | 3.5 | 3.5 | 0.05 | 0.5 | |
|  | Potassium hydroxide | | | | | 0.38 | | | | | 0.3 |
| H | L-glutamic acid | | | | | | | | | | 0.06 |
|  | Phosphoric acid | | | 0.3 | 0.2 | 0.2 | 2 | 3 | 0.3 | 0.3 | 0.05 |
| D | N-(hexadecyloxyhydroxypropyl)-N-hydroxyethylhexadecanamide | | | | | | 10 | 10 | 0.1 | | |
|  | Ceramide (type 2) | | | | | | | | | 1 | 1 |
| E | Cholesterol | | | | | | 0.01 | 5 | 0.1 | 0.5 | 0.5 |
|  | Cholesteryl isostearate | | | | | | | | | | |
| F | Stearic acid | | | | | | 5 | 0.3 | | | |
|  | Squalane | | | | | | | | | | |
|  | Dimethylpolysiloxane | | | | | | | | | | |
|  | Cetanol | | | | | | | | | | |
|  | 1,3-butylene glycol | 8.06 | | | | | | | | | |
|  | Glycerin | | | | | | | | | 5 | 5 |
|  | Carboxyvinyl polymer | | | | | | | | | | |
|  | Hydroxyethyl(hydroxypropylpolyethyleneglycol dodecyl ether) cellulose | 2.69 | | | | | | | | | |
|  | O-[2-hydroxy-3-(trimethylammonio)propyl]hydroxyethyl cellulose chloride | | | | | | | | | | |
|  | Methyl paraoxybenzoate | | | | | | | | | | |
| C | Ion exchange water | Balance | Balance | Balance | Balance | Balance | Balance | Balance | Balance | Balance | Balance |
| Total | | 100 | 100 | 100 | 100 | 100 | 100 | 100 | 100 | 100 | 100 |
| pH: At the time of preparation | | 6.3 | 9.2 | 9.2 | 3.9 | 3 | 2 | 9.3 | 2.4 | 9.6 | 3.9 |
| After component (G) or (H) was added after preparation | | | | 3.9 | | 11.2 | 6.4 | 3.3 | 8.5 | 3.9 | 8.7 |
| State of vesicle immediately after preparation | | A | A | A | A | A | A | A | A | A | A |
| State of vesicle after pH was changed immediately after preparation | | | A | | A | A | A | A | A | B | B |
| Storage stability: 50° C. | | A | A | A | A | A | A | A | A | C | C |
| 25° C. | | A | A | A | A | A | A | A | A | C | C |
| 5° C. | | A | A | A | A | A | A | A | A | C | C |
| Adaptability upon application (the number of panelists who evaluated as "adaptable") | | 5 | 5 | 5 | 5 | 5 | 6 | 6 | 5 | 2 | 4 |

Experimental Example 1

Water retention amount was evaluated with respect to compositions of Examples 1, 2, 3, 6, and 18 and Comparative Example 2. The results are shown in Table 2.

(Evaluation Method)

The water content of the skin was measured as follows. Three sites of the front arm were determined. Water contents were measured at four points in the vicinity of each of the three sites, that is, 12 points in total, by Corneometer (CORNEOMETER CM825, manufactured by Integral Corporation). Numerical values displayed on the Corneometer were used as the water content. First, the front arm was washed with a face-wash (Biore face-wash foam, manufactured by Kao Corp.). Ten minutes after water was removed, water content was measured. This was regarded as an initial value. Next, each composition was applied in the morning and after bathing. This procedure was repeated for 3 days. Three days later, the front arm was washed with the above face-wash. Ten minutes after water was removed, water content was measured. The numerical value obtained by subtracting the initial value from the measurement value of water-content after three days was regarded as a water retention amount. An average value of water retention amounts of 12 points in total was determined as a water retention amount of each composition.

thereby producing a vesicle composition comprising components (A), (B), (C) and at least one of component (G) and component (H):

(A) 0.0001 to 20 mass % of an organic acid represented by formula (1):

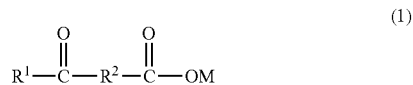

where $R^1$ represents a natural sterol having a single hydroxy group or a hydrogenated product thereof or a residue which remains after a hydrogen atom is removed from the hydroxy group of bile acid, $R^2$ represents a divalent hydrocarbon group having 1 to 24 carbon atoms, M represents a hydrogen atom, an alkali metal, an alkali earth metal, ammonium, an alkanolammonium having 2 to 9 carbon atoms in total, an alkylammonium or alkenylammonium having 1 to 22 carbon atoms in total, pyridinium substituted with an alkyl group or alkenyl group having 1 to 18 carbon atoms or a basic amino acid, (B) 0.0001 to 10 mass % of a sphingosine, (C) water, and at least one of: (G) a base other than component (B), and (H) an acid other than component (A), wherein said vesicle composition has a pH of from 2 to 11.

TABLE 2

| | Component (mass %) | Example 1 | Example 2 | Example 3 | Example 6 | Example 18 | Comp. Ex. 2 |
|---|---|---|---|---|---|---|---|
| A | n-Octadecenylsuccinic acid cholesteryl monoester | 1 | 1 | 1 | 1.25 | | |
| | n-Hexadecenylsuccinic acid cholesteryl monoester | | | | | 0.05 | |
| B | Phytosphingosine (manufactured by COSMOFERM) | 0.1 | 0.1 | 0.1 | 0.05 | | 0.1 |
| | Pseudo sphingosine (ii) | | | | | 1 | |
| G | L-arginine | 0.5 | 0.5 | | | 0.05 | |
| | Potassium hydroxide | | | | | | 0.3 |
| H | L-glutaminic acid | | | 0.06 | 0.05 | | 0.06 |
| | Phosphoric acid | | 0.3 | 0.05 | | 0.3 | 0.05 |
| D | N-(hexadecyloxyhydroxypropyl)-N-hydroxyethylhexadecanamide | | | | 1 | 0.1 | |
| | Ceramide (type 2) | 1 | 1 | 1 | | | 1 |
| E | Cholesterol | 0.5 | 0.5 | 0.5 | 0.25 | 0.1 | 0.5 |
| | Cholesteryl isostearate | | | | 0.1 | | |
| F | Stearic acid | | | | 0.1 | | |
| | Squalane | | | | 0.5 | | |
| | Dimethylpolysiloxane | | | | 1 | | |
| | Cetanol | | | | 0.2 | | |
| | 1,3-Butylene glycol | | | | 5 | | |
| | Glycerin | 5 | 5 | 5 | 10 | | 5 |
| | Hydroxyethyl(hydroxypropylpolyethylene glycol dodecyl ether)cellulose | | | | 0.15 | | |
| | O-[2-hydroxy-3-(trimethylammonio)propyl]hydroxyethylcellulose chloride | | | | 0.5 | | |
| | Methyl paraoxybenzoate | | | | 0.2 | | |
| C | Ion exchange water | Balance | Balance | Balance | Balance | Balance | Balance |
| | Total | 100 | 100 | 100 | 100 | 100 | 100 |
| | Water retention amount | 14.2 | 13.9 | 14.8 | 19.7 | 7.5 | 2.7 |

As the results shown in Table 2, the water retention amount of Examples were high compared to Comparative Examples. It is considered that the skin permeability of the compositions of Examples is extremely high regardless of pH.

The invention claimed is:

1. A method, comprising:

mixing an oil phase comprising a component (A) and a component (B) with heating;

dissolving a component (G) or a component (H) in part of a component (C) to form a first solution, adding the first solution to said oil phase and mixing the first solution and the oil phase to form a second solution;

cooling said second solution; and mixing a water phase comprising the remaining part of said component (C) to said second solution to form a vesicle composition and stirring the vesicle composition, 2. The method according to claim 1, wherein said second solution obtained by adding the first solution which is obtained by dissolving component (G) in part of component (C) to said oil phase and mixing them has a pH of greater than 5.5, and, after said mixing, the method further comprises dissolving component (H) in a part of component (C)

to form said vesicle composition, thereby controlling the pH of the vesicle composition to a value of from 2 to 11.

3. The method according to claim 1, wherein said second solution obtained by adding the first solution which is obtained by dissolving component (H) in part of component (C) to said oil phase and mixing them a pH 5.5 or less, and, after said mixing, the method further comprises dissolving component (G) in a part of component (C) to form said vesicle composition, thereby controlling the pH of the vesicle composition to a value of from 2 to 11.

4. The method of claim 2, wherein said second solution comprises component (A) in an ionized form with component (B) as a co-surfactant, and, after dissolving component (H) in a part of component (C) to form said vesicle composition, said vesicle composition comprises component (B) in cationized form with component (A) as a co-surfactant.

5. The method of claim 3, wherein said second solution comprises component (B) in cationized form with component (A) as a co-surfactant, and, after dissolving component (G) in a part of component (C) to form said vesicle composition, said vesicle composition comprises component (A) in anionized form with component (B) as a co-surfactant.

6. The method of claim 1, wherein the vesicle composition comprising components (A), (B), (C) and at least one of component (G) and component (H) retains the presence of vesicles and does not precipitate crystals after storage at 50° C. for one week.

7. The method of claim 1, wherein the vesicle composition comprising components (A), (B), (C) and at least one of component (G) and component (H) retains the presence of vesicles and does not precipitate crystals after storage at 25° C. for one week.

8. The method of claim 2, wherein said second solution obtained by adding the first solution which is obtained by dissolving component (G) in part of component (C) to said oil phase and mixing them has a pH of greater than 7.

9. The method of claim 1, capable of pH adjustment of from pH of 2 to pH of 11.2 without disappearance of vesicles.

10. The method of claim 1, capable of pH adjustment of from pH of 3 to pH of 11.2 without disappearance of vesicles.

11. The method of claim 1, wherein, in the vesicle composition comprising components (A), (B), (C) and at least one of component (G) and component (H), component (A) is present in an amount of from 0.01 to 10 mass %.

12. The method of claim 1, wherein, in the vesicle composition comprising components (A), (B), (C) and at least one of component (G) and component (H), component (B) is present in an amount of from 0.01 to 2 mass %.

13. The method of claim 1, wherein, in the vesicle composition comprising components (A), (B), (C) and at least one of component (G) and component (H), component (A) is present in an amount of from 0.01 to 10 mass % and component (B) is present in an amount of from 0.01 to 2 mass %.

* * * * *